United States Patent
Kim et al.

(10) Patent No.: US 11,690,887 B2
(45) Date of Patent: Jul. 4, 2023

(54) **COMPOSITION FOR AMELIORATING PSORIASIS SYMPTOMS CONTAINING EXTRACT OF *DIANTHUS SUPERBUS* L**

(71) Applicant: KOREA INSTITUTE OF SCIENCE AND TECHNOLOGY, Seoul (KR)

(72) Inventors: Jin Chul Kim, Gangneung-si (KR); Dorjsembe Banzragch, Gangneung-si (KR); Eun Ha Lee, Gangneung-si (KR); Sung Chul Hong, Gangneung-si (KR); Jung Yeob Ham, Gangneung-si (KR); Tae Jung Kim, Gangneung-si (KR); Chu Won Nho, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/205,498

(22) Filed: Mar. 18, 2021

(65) Prior Publication Data

US 2022/0080013 A1   Mar. 17, 2022

(30) Foreign Application Priority Data

Sep. 14, 2020   (KR) .................. 10-2020-0117911

(51) Int. Cl.

| | | |
|---|---|---|
| *A61K 36/36* | (2006.01) | |
| *A23L 33/105* | (2016.01) | |
| *A61K 8/9789* | (2017.01) | |
| *A61K 9/20* | (2006.01) | |
| *A61K 9/00* | (2006.01) | |
| *A61K 9/08* | (2006.01) | |
| *A61P 17/06* | (2006.01) | |
| *A61K 9/14* | (2006.01) | |

(52) U.S. Cl.
CPC ............ *A61K 36/36* (2013.01); *A23L 33/105* (2016.08); *A61K 8/9789* (2017.08); *A61K 9/0019* (2013.01); *A61K 9/08* (2013.01); *A61K 9/14* (2013.01); *A61K 9/20* (2013.01); *A61P 17/06* (2018.01); *A61K 2236/33* (2013.01); *A61K 2236/50* (2013.01)

(58) Field of Classification Search
None
See application file for complete search history.

(56) References Cited

U.S. PATENT DOCUMENTS

| | | |
|---|---|---|
| 2016/0367570 A1 | 12/2016 | Dow et al. |
| 2017/0225006 A1 | 8/2017 | Anderson et al. |

FOREIGN PATENT DOCUMENTS

| | | | | |
|---|---|---|---|---|
| CN | 105169222 A | * | 12/2015 | |
| CN | 106902275 A | * | 6/2017 | |
| CN | 108324816 A | * | 7/2018 | ........... A61K 31/352 |
| JP | 2000-53557 A | | 2/2000 | |
| JP | 2000103718 A | * | 4/2000 | |
| KR | 10-2000-0064607 A | | 11/2000 | |
| KR | 10-1781579 B1 | | 9/2017 | |
| KR | 10-2018-0053292 A | | 5/2018 | |
| KR | 10-2018-0114246 A | | 10/2018 | |
| KR | 10-2018-0134856 A | | 12/2018 | |
| KR | 10-2019-0137329 A | | 12/2019 | |
| KR | 10-2020-0060837 A | | 6/2020 | |
| WO | WO 97/34644 A1 | | 9/1997 | |

OTHER PUBLICATIONS

Hsieh (Chem. Pharm. Bull. (2005), vol. 53, No. 3, pp. 336-338).*
"Healing Waters Clinic" webpage (https://healingwatersclinic.com/product/dianthus-qu-mai/—accessed Sep. 2022).*
"Qu Mai" webpage (https://www.bioessence.com/home/productdetail/100435—accessed Sep. 2022).*

* cited by examiner

*Primary Examiner* — Susan Hoffman
(74) *Attorney, Agent, or Firm* — Birch, Stewart, Kolasch & Birch, LLP (57) ABSTRACT

Disclosed is a composition for ameliorating, preventing or treating an autoimmune skin disease, containing a super pink (*Dianthus superbus* L.) extract as an active ingredient.

6 Claims, 8 Drawing Sheets

COMPOSITION FOR AMELIORATING PSORIASIS SYMPTOMS CONTAINING EXTRACT OF *DIANTHUS SUPERBUS* L

CROSS-REFERENCE TO RELATED APPLICATION

This application claims under 35 U.S.C. § 119(a) the benefit of priority to Korean Patent Application No. 10-2020-0117911 filed on Sep. 14, 2020, the entire contents of which are incorporated herein by reference.

BACKGROUND

(a) Technical Field

The present invention relates to a composition for ameliorating, preventing or treating an autoimmune skin disease, particularly psoriasis, containing an extract of *Dianthus superbus* L.

(b) Background Art

Psoriasis is a common autoimmune skin disease characterized by papules along with silvery white scales and causes a wide variety of symptoms such as systemic exfoliation, erythema, itching, dryness and burning sensation, wherein the distribution and degree thereof vary depending on the individual. Psoriasis occurs worldwide, but has remarkable differences in the frequency of incidence between races and ethnic groups, and the clinical course may vary, but generally continues along a course of repeated amelioration and worsening. Although the pathogenesis of psoriasis has not been completely elucidated, research results have been reported stating that psoriasis is caused by factors such as invasion of inflammatory cells, an increased number of immune activation molecules, Th1 and Th17 responses, and abnormal changes in inflammation-related cytokines, and thus inflammation is a pathogenic determinant.

Psoriasis is a chronic recurrent disease and thus should be treated using a method that is capable of exhibiting superior effects and minimal side effects. Known psoriasis therapies are broadly categorized as local therapy, systemic therapy, phototherapy, and treatment using biological agents. It is generally common for local therapy to be performed for mild cases, but a combination of local therapy with ultraviolet therapy or systemic therapy is performed for severe cases.

However, there are not many known natural functional agents used in the treatment of psoriasis.

The above information disclosed in this Background section is only for enhancement of understanding of the background of the invention, and therefore it may contain information that does not form the prior art that is already known in this country to a person of ordinary skill in the art.

PRIOR ART DOCUMENT

Patent Document (Patent Document 1) Korean Patent Laid-open No. 10-2000-0064607
(Patent Document 2) Korean Patent Laid-open No. 10-2018-0134856
(Patent Document 3) Korean Patent Laid-open No. 10-2018-0053292

SUMMARY OF THE DISCLOSURE

In order to solve the above-described problems associated with the prior art, while searching for a composition for preventing and treating psoriasis from natural products, the present inventors found that, by administering a *Dianthus superbus* L. extract, the *Dianthus superbus* L. extract can be used as a means for ameliorating psoriasis through phototherapy using natural products based on the increased water amount, decreased water loss, and suppression of skin morphological changes and inflammation expression. Based on this finding, the present invention has been completed.

Accordingly, it is one object of the present invention to provide a pharmaceutical composition for ameliorating, preventing or treating an autoimmune skin disease containing a *Dianthus superbus* L. extract as an active ingredient, a kit containing the pharmaceutical composition, and a method of ameliorating or treating an autoimmune skin disease, particularly, psoriasis including administering the pharmaceutical composition.

The objects of the present invention are not limited to those described above. The objects of the present invention will be clearly understood from the following description, and can be implemented by the means defined in the claims and combinations thereof.

In order to achieve the above object, the present invention provides the following composition.

In one aspect, the present invention provides a composition for ameliorating, preventing or treating an autoimmune skin disease, containing a super pink extract as an active ingredient.

In one aspect of the present invention, the super pink is *Dianthus superbus* L., and the *Dianthus superbus* L. extract is an extract of water, a $C_1$-$C_6$ alcohol, or a $C_1$-$C_6$ alcohol aqueous solution.

In one aspect of the present invention, the concentration of the $C_1$-$C_6$ alcohol aqueous solution is 10% to 90% (v/v).

In one aspect of the present invention, the *Dianthus superbus* L. extract is an extract of the aboveground or underground portion of *Dianthus superbus* L., and the *Dianthus superbus* L. extract is an methanol extract.

In one aspect of the present invention, the autoimmune skin disease is psoriasis.

In an embodiment, the composition prevents, ameliorates or treats psoriasis by reducing skin moisture loss due to psoriasis, increasing skin moisture, reducing a change in skin thickness due to psoriasis, or reducing the size of a skin area exhibiting redness due to psoriasis.

In an embodiment, the composition prevents, ameliorates or treats psoriasis by inhibiting one or more inflammatory cytokines selected from IL-1β, IL-23p19, TNF-α, CCL20, CXCL8, S100A7, S100A8, and S100A9.

In one aspect of the present invention, the composition is a health functional food.

In one aspect of the present invention, the composition is a pharmaceutical composition.

In one aspect of the present invention, the composition is a functional cosmetic composition.

Other aspects and preferred embodiments of the invention are discussed infra.

BRIEF DESCRIPTION OF THE DRAWINGS

The above and other features of the present invention will now be described in detail with reference to certain exemplary embodiments thereof, illustrated in the accompanying drawings which are given hereinbelow by way of illustration only, and thus are not limitative of the present invention, and wherein.

DETAILED DESCRIPTION

Unless the context clearly indicates otherwise, all numbers, figures and/or expressions that represent ingredients, reaction conditions, polymer compositions and amounts of mixtures used in the specification are approximations that reflect various uncertainties of measurement occurring inherently in obtaining these figures, among other things. For this reason, it should be understood that, in all cases, the term "about" should modify all numbers, figures and/or expressions. In addition, when numerical ranges are disclosed in the description, these ranges are continuous and include all numbers from the minimum to the maximum, including the maximum within the range, unless otherwise defined. Furthermore, when the range refers to an integer, it includes all integers from the minimum to the maximum, including the maximum within the range, unless otherwise defined.

It should be understood that, in the specification, when a range is referred to regarding a parameter, the parameter encompasses all figures including end points disclosed within the range. For example, the range of "5 to 10" includes figures of 5, 6, 7, 8, 9, and 10, as well as arbitrary sub-ranges, such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include numbers such as 10%, 11%, 12% and 13% as well as 30%, and any sub-ranges of 10% to 15%, 12% to 18%, or 20% to 30%, as well as any numbers, such as 10.5%, 15.5% and 25.5%, between appropriate integers that fall within the range.

Hereinafter, the present invention will be described in detail.

In one aspect, the present invention provides a composition for ameliorating, preventing or treating an autoimmune skin disease, containing a super pink extract as an active ingredient.

As used herein, the term "*Dianthus superbus* L." is a perennial plant belonging to Caryophyllaceae. It grows to about 1 m in height, has no hair, and is green speckled with white. Leaves are linear-lanceolate, have sharp tips and leaf bases that join to surround the nodes, and are around 10 cm in length. Flowers are pink and form inflorescences, and the diameter is about 5 mm. The calyx has a long cylindrical structure and a length of 3 cm or more, and is 5-lobed at the apex and is lanceolate.

In one aspect of the present invention, the super pink may be *Dianthus superbus* L.

The *Dianthus superbus* L. extract may be extracted from various organs of natural, hybrid and mutant plants, for example, roots, stems, leaves, flowers, trunks of fruits, skins of fruits, as well as plant tissue cultures, preferably roots and stems. The *Dianthus superbus* L. extract of the present invention may be a solvent extract extracted with an extraction solvent, a fraction obtained by adding a fractionation solvent to an extract prepared by extraction with an extraction solvent, or a purified product obtained from the fraction through chromatography. The extraction solvent may be water, an organic solvent, or a mixed solvent thereof that can be used to extract natural products. The extraction solvent may be water, an alcohol having 1 to 6 carbon atoms, or a mixture thereof, such as water or ethanol. The *Dianthus superbus* L. extract of the present invention may be prepared according to a conventional method for producing a plant extract. More specifically, the preparation of the *Dianthus superbus* L. extract may be carried out by removing impurities from stems and roots of *Dianthus superbus* L., drying the *Dianthus superbus* L. stems and roots, pulverizing the dried product and extracting the pulverized product using an extraction solvent. The extraction using the solvent may be cold extraction, warm extraction, solubilization extraction, reflux extraction, or ultrasonic-assisted extraction.

As used herein, the term "fraction" means a result obtained by performing fractionation in order to separate a specific component or a specific group of components from a mixture containing various components.

In addition, the preparation of the fraction of the extract may be carried out by adding a fractionation solvent to the extract prepared by the extraction method, followed by obtaining a fraction depending on the polarity of the fractionation solvent. The method of obtaining the fraction may be performed by fractionation or separation through layer separation. More specifically, fractionation solvents, for example, ethyl acetate and water, are added to the extract in the same order as described above, and then layer-separated ethyl acetate fraction and water fraction are obtained. The fractionation through layer separation may include sequentially adding solvents to the extract according to the degree of non-polarity of the solvents and obtaining a fraction through layer separation during each application. For example, an ethyl acetate fraction is obtained by adding ethyl acetate to an aqueous ethanol extract and fractionating the layer-separated ethyl acetate layer, and then a water fraction is obtained as the layer left behind after separating the ethyl acetate fraction. The chromatography method used for purification of the fractions may be selected from among various chromatography methods such as silica gel column chromatography, thin-layer chromatography (TLC) and high-performance liquid chromatography (HPLC).

In one aspect of the present invention, the super pink is *Dianthus superbus* L., and the *Dianthus superbus* L. extract is an extract of water, a $C_1$-$C_6$ alcohol, or a $C_1$-$C_6$ alcohol aqueous solution.

In one aspect of the present invention, the concentration of the $C_1$-$C_6$ alcohol aqueous solution is 10% to 90% (v/v).

In one aspect of the present invention, the *Dianthus superbus* L. extract is an extract of the aboveground or underground portion of *Dianthus superbus* L., and the *Dianthus superbus* L. extract is an methanol extract.

The $C_1$-$C_6$ alcohol may be methanol, ethanol, propanol, butanol, pentanol, or hexanol. In addition, the $C_1$-$C_6$ aqueous alcohol solution may have a concentration of 5 to 99%. In a preferred embodiment, the extraction solvent may be methanol.

In one aspect of the present invention, the autoimmune skin disease is psoriasis, lupus or atopic dermatitis.

In one aspect of the present invention, the autoimmune skin disease is psoriasis.

"Psoriasis" causes symptoms such as systemic exfoliation, erythema, itching, dryness and burning sensation.

In one aspect of the present invention, the composition ameliorates or treats psoriasis by reducing skin moisture loss due to psoriasis, increasing skin moisture, reducing a change in skin thickness due to psoriasis, or reducing the size of a skin area exhibiting redness due to psoriasis.

In one aspect of the present invention, the composition prevents psoriasis by inhibiting one or more inflammatory cytokines selected from IL-1β, IL-23p19, TNF-α, CCL20, CXCL8, S100A7, S100A8, and S100A9.

In one embodiment, the pharmaceutical composition of the present invention may increase the amount of moisture in the skin or suppress the change in the thickness of the ear and skin epithelium and the expression of inflammation. The change in the shape of the skin causes an increase in the thickness of the ear and the skin surface compared to the normal control group due to the inflammatory response and causes the expression of inflammation due to the increase in the number of inflammatory cells and T cells according to the inflammatory reaction. The composition of the present invention can inhibit and ameliorate these phenomena. In one embodiment of the present invention, after treatment with the *Dianthus superbus* L. extract or a fraction thereof, and completion of the experiment, the fraction-treatment group was found to exhibit a reduced damaged area, a significantly increased amount of moisture in the skin, and decreased moisture loss compared to the psoriasis-inducing group. In addition, it was found that inflammation expression was reduced at the levels of protein and RNA.

In one aspect of the present invention, the composition is a pharmaceutical composition.

The carrier, excipient and diluent that can be contained in the pharmaceutical composition of the present invention include one or more selected from lactose, dextrose, sucrose, sorbitol, mannitol, xylitol, erythritol, maltitol, starch, gum acacia, alginate, gelatin, calcium phosphate, calcium silicate, cellulose, methyl cellulose, hydroxymethyl cellulose, microcrystalline cellulose, silicified microcrystalline cellulose, povidone, crospovidone, croscarmellose sodium, polyvinylpyrrolidone, water, methylhydroxybenzoate, propylhydroxybenzoate, Neusilin, colloidal silicon dioxide, lactose, talc, magnesium stearate, colloidal magnesium stearyl, and mineral oil.

The treatment amount of the pharmaceutical composition of the present invention is determined in consideration of other factors well known in the medical field, such as the purpose of use, disease severity, age, weight, state of health, gender, sensitivity to drugs, treatment time, treatment route, or type of substance used as an active ingredient. The composition may contain a *Dianthus superbus* L. extract or a fraction thereof as a single active ingredient. That is, the composition may not contain a single active ingredient other than the *Dianthus superbus* L. extract or a fraction thereof. In one embodiment, there is provided a method for treating psoriasis in a subject, including treating the subject with the pharmaceutical composition in an amount effective to prevent or treat psoriasis. The subject may be a mammal. The mammal may be a human, dog, cat, cow, goat, or pig. In addition, the subject may be a human or an animal other than a human, and may be a human or a mammal other than a human. The treatment can be carried out through any general route, as long as the composition is capable of reaching the target tissue. For example, the subject may be treated through a route such as skin application, intraperitoneal administration, intravenous administration, intramuscular administration, subcutaneous administration, intradermal administration, transdermal patch, oral administration, intranasal administration, intrapulmonary administration, and rectal administration. Specifically, the subject can be treated as desired through a route such as skin application. Preferably, the subject is treated through a skin application route. The preferred dosage of the pharmaceutical composition of the present invention varies depending on the patient's age, weight, severity of disease, drug form, administration route and administration duration, but may be appropriately selected by those skilled in the art. However, for a desirable effect, the pharmaceutical composition of the present invention may be administered at a dosage of 0.001 mg/kg to 1 mg/kg per day, preferably 0.1 mg/kg to 10 mg/kg per day. The administration may be performed several times a day, preferably in a portionwise manner once to six times, at regular time intervals, according to the determination of a doctor or pharmacist.

In another aspect, the present invention provides a kit containing the pharmaceutical composition according to any one of the aspects of the present invention.

In another aspect, the present invention provides a method of ameliorating or treating an autoimmune skin disease in a subject, the method including administering the pharmaceutical composition according to any one of the aspects of the present invention to the skin through skin application.

In yet another aspect of the present invention, the subject is an animal other than a human.

In yet another aspect of the present invention, the autoimmune skin disease is psoriasis.

In one aspect of the present invention, the composition is a health functional food.

The health food composition of the present invention contains the *Dianthus superbus* L. extract or a solvent fraction fractionated therefrom, and there is no particular limitation on the kind thereof. Examples of the food include drinks, meat, sausages, bread, biscuits, rice cakes, sunsik (Korean ready-to-eat food prepared from grains), chocolate, candy, snacks, confectioneries, pizza, ramen, other noodles, gums, dairy products including ice cream, various soups, beverages, alcoholic beverages, vitamin complexes, dairy products and processed dairy products, and include all other functional health foods in the conventional sense. As an active ingredient, the extract of *Dianthus superbus* L. or the solvent fraction fractionated therefrom may be added alone to the food or may be used in conjunction with other foods or food ingredients, and may be suitably used according to conventional methods. The effective content may be appropriately determined according to the purpose of use (for prevention or amelioration), and may be present in a range of 0.001 to 70% by weight with respect to the total weight of the health food. However, in the case of long-term intake for health and hygiene purposes or for health control, the amount may be below the above range, and the active ingredient may be used in an amount above the range, since there is no problem in terms of safety. For example, in the case of preparing health beverages, the health drink may contain, in addition to the active ingredient, natural carbohydrates or flavoring agents as additives commonly used in the preparation of beverages. The natural carbohydrates may include conventional sugars, such as monosaccharides (e.g. glucose, fructose, etc.), disaccharides (e.g. maltose, sucrose, etc.) and polysaccharides (e.g., dextrin, cyclodextrin, etc.), as well as sugar alcohols such as xylitol, sorbitol and erythritol. The natural carbohydrate may be present in a range of 1 to 20% by weight, preferably to 10% by weight, with respect to the total weight of the health food. The flavoring agent may include natural flavoring agents (thaumatin, *stevia* extract, rebaudioside A, glycyrrhizin, etc.) and synthetic flavoring agents (saccharin, aspartame, etc.). The health food may contain other nutrients, vitamins, minerals (electrolytes), flavors (synthetic or natural flavors), colorants, pectic acids and salts thereof, alginic acids and salts thereof, organic acids, protective colloidal thickeners, pH-adjusting agents, stabilizers, preservatives, glycerin, alcohol, carbonic acid used in carbonated beverages, and the like. In addition, it may contain flesh for the production of natural fruit juices, fruit juice beverages and vegetable beverages. The content of these additives is not particularly limited, but may fall within a range of 0.1 to 20% by weight with respect to the total weight of the health food.

In one aspect of the present invention, the composition may be a functional cosmetic composition. In one aspect of the present invention, the composition may be formulated in the form of any one of powders, granules, tablets, capsules, suspensions, emulsions, syrups, aerosols and external preparations. In one aspect of the present invention, the composition may be a cosmetic composition. The cosmetic composition of the present invention may be prepared in any one of formulations conventionally prepared in the art, for example, solutions, suspensions, emulsions, pastes, gels, creams, lotions, powders, soaps, surfactant-containing cleansings, oils, powder foundations, emulsion foundations, wax foundations and spray, but is not limited thereto.

Hereinafter, the present invention will be described in more detail with reference to specific examples. However, the following examples are provided only for illustration of the present invention, and should not be construed as limiting the scope of the present invention.

EXAMPLE

Example 1. Preparation of *Dianthus superbus* L. Extract

*Dianthus superbus* L. used in this example was collected from Ulantabot, Mongolia.

1-1. Preparation of Methanol Extract 1.5 L of methanol was added to 500 g of flowers, leaves and stems of *Dianthus superbus* L., and the resulting mixture was allowed to stand three times at room temperature for 48 hours. The resulting solution was filtered through filer paper and the resulting filtrate was distilled under reduced pressure to obtain 25 g of an extract.

Figure 1:
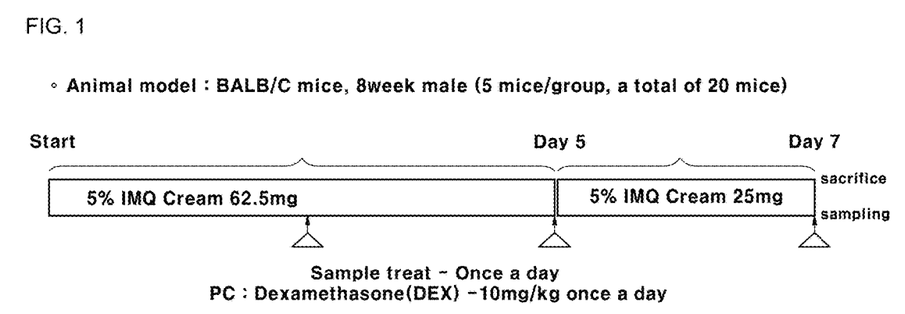
FIG. 1 shows a schematic experimental scheme of an animal model.

Example 2: Efficacy Evaluation Using Experimental Animals 2-1. Production of Psoriasis Animal Model 6-week-old male Balb/c mice (Kangwon Life Science, Korea) were purchased and acclimated for a week, and psoriasis was induced using 5% imiquimod (Donga ST, Korea). FIG. 1 is a schematic experimental scheme of an animal model. Anti-psoriatic efficacy was investigated using a total of 20 animal models including 5 animals per experimental group.

2-2. Animal Experiment Design

In order to determine the effect of the extract of *Dianthus superbus* L. on psoriasis caused by imiquimod, the experimental animals of Section 2-1 were used. The following four experimental groups were constructed and five animals were randomly assigned to each group:

Normal control without any treatment (Non-treatment control, NTC);

Disease group with psoriasis induced using imiquimod by the method of Section 2-1 (IMQ);

Group to the skin of which dexamethasone was applied every day after induction of psoriasis (Positive control, DEX); and Group to the skin of which the extract of *Dianthus superbus* L. of Example 1 was applied (Experimental group, M1)

Figure 2:
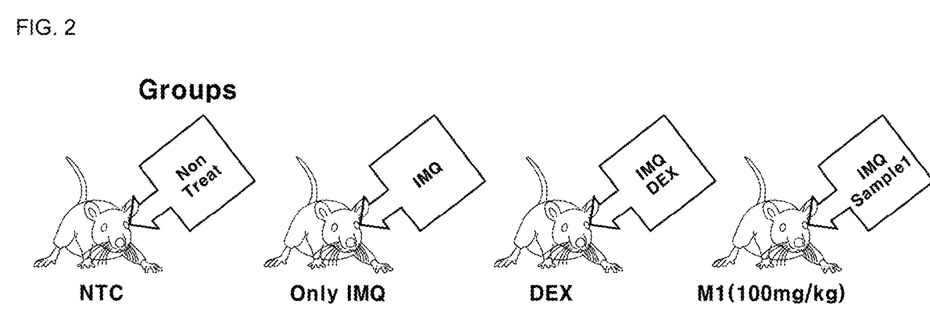
FIG. 2 is a schematic diagram showing four groups in Example 2-2 of the present invention.
Figure 3:
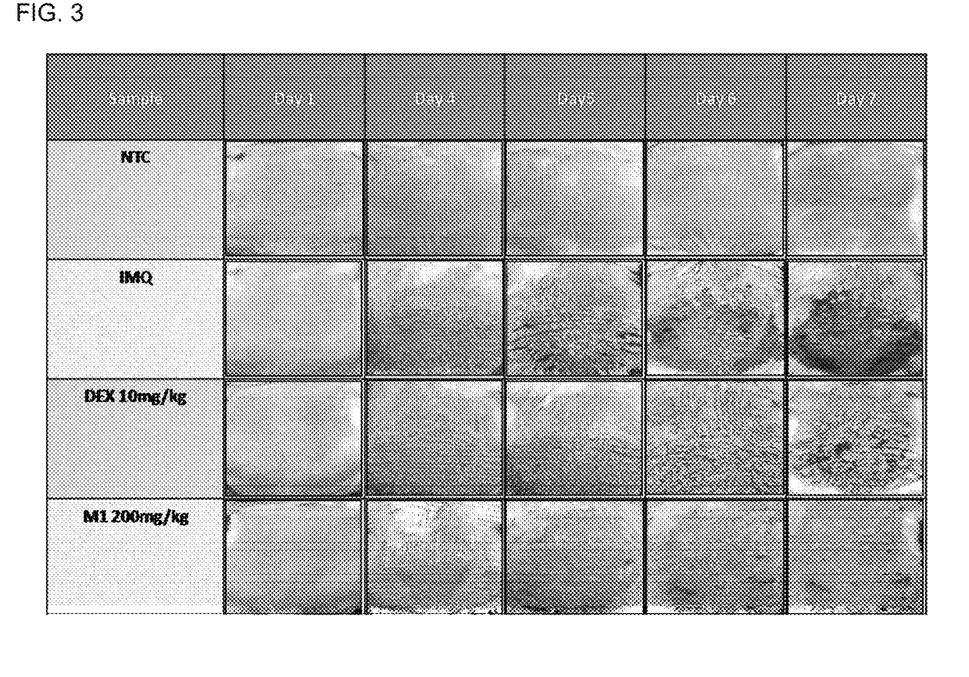
FIG. 3 is an image showing a change over 7 days in a psoriasis-induced model as an animal experimental model in Example 2-2 of the present invention.

The experiment was conducted by inducing psoriasis with IMQ cream and then performing daily application in the amount shown in FIG. 2 to the experimental group and the DEX group. FIG. 3 is an image showing the treatment group for 7 days compared to the psoriasis-induced model as the animal experimental model.

2-3. Verification of Effects of Improving Epithelial Thickness and Inflammation of the Back Through Tissue Staining After treatment for a week, the back skin tissue was removed from each animal, and then a paraffin block was prepared. The paraffin block was cut to 5 μm to prepare a slide sample, and then the change in the thickness of the skin tissue was measured through H&E staining.

Figure 4:
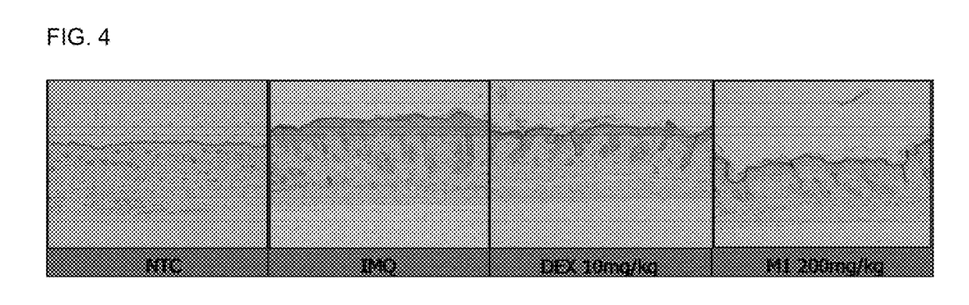
FIGS. 4 and 5 show results of Example 2-3 of the present invention.
Figure 5:
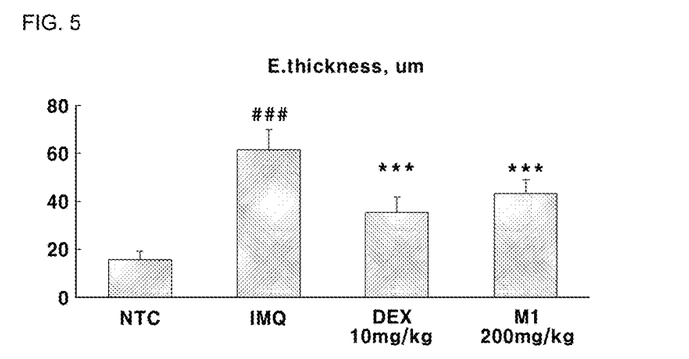

The experimental results are shown in FIGS. 4 and 5.

The results show that the psoriasis-induced IMQ group had increased thickness of the epithelial layer, whereas the DEX group and the *Dianthus superbus* L. extract treatment group had decreased thickness thereof compared to the IMQ group.

2-4. Verification of Effect of Improving Epithelial Tissue Damage to Back Skin Tissue Through Immunofluorescence After treatment for a week, back skin tissue was removed from each animal and a paraffin block was then prepared. A paraffin block was cut to 5 μm to prepare a slide sample, and then the change in biomarkers for epithelial tissue damage due to psoriasis was measured through immunofluorescence.

Figure 6:
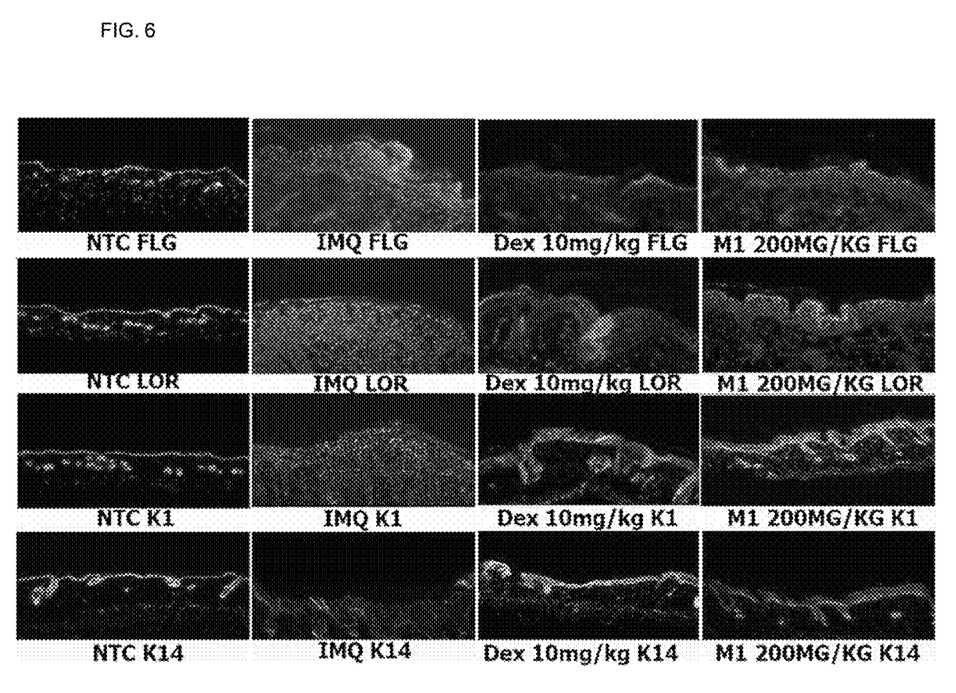
FIG. 6 shows a result of Example 2-4 of the present invention.
Figure 7A:
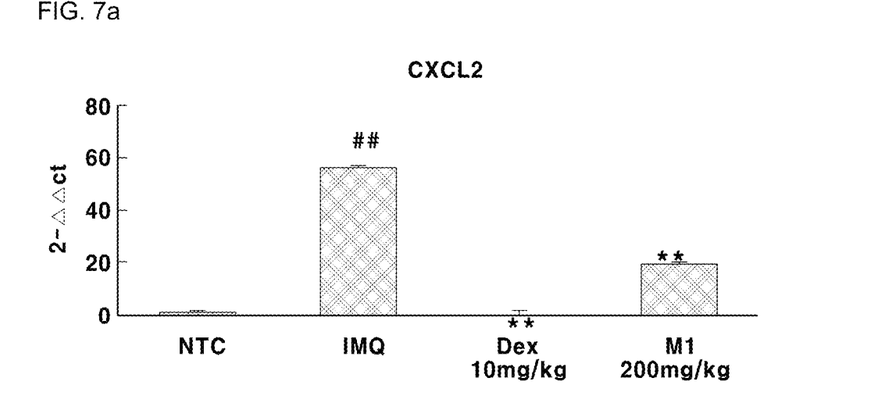
FIG. 7a-7d shows a result of Example 2-5 of the present invention.
Figure 7B:
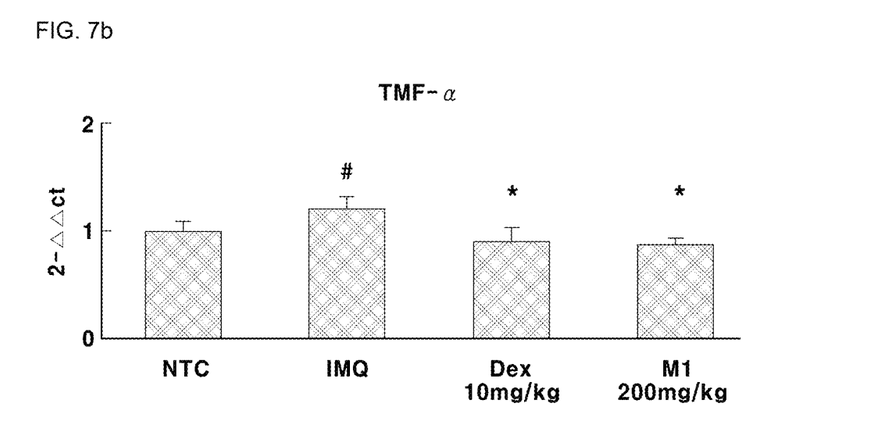
Figure 7C:
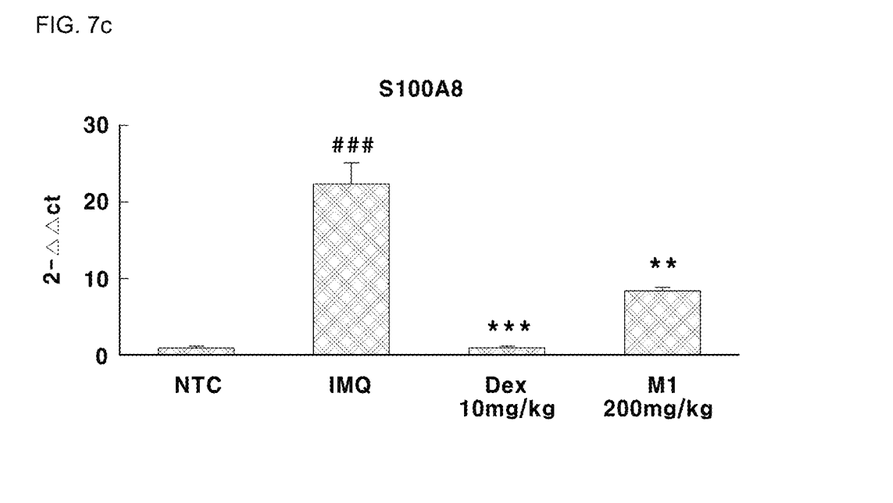
Figure 7D:
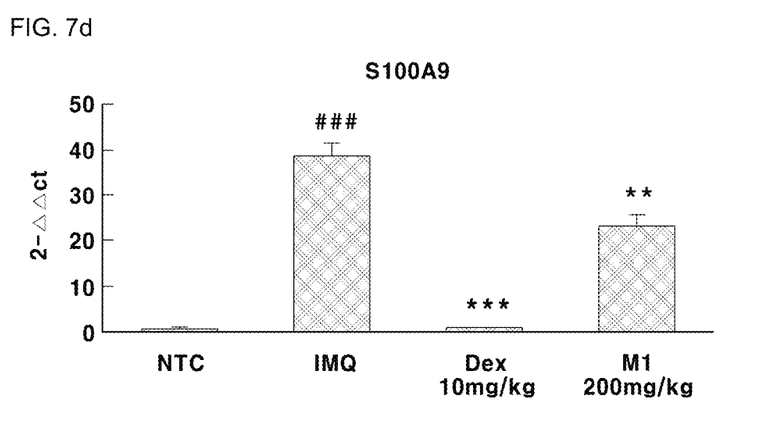

The experimental results are shown in FIG. 6.

The results show that the expression levels of filaggrin, loricrin, keratin 1 and keratin 14 decreased in the psoriasis-induced IMQ group compared to the non-treatment group, whereas the expression levels of filaggrin, loricrin, keratin 1, and keratin 14 in the *Dianthus superbus* L. extract treatment group increased, like the DEX group.

2-5. Effects of Improving Inflammation at RNA Level Through Animal Testing 200 mg of the extracted tissue was precisely weighed, and then 400 μL of a buffer (100 mM Tri-HCl, 250 mM sucrose pH 7.4) was added thereto, followed by homogenization. After homogenization, the resulting product was centrifuged in a new tube at 10,000×g for 10 minutes. The intermediate layer, excluding the upper and lower layers of debris, was isolated and used as a sample.

The contents of CXCL2, TNF-α, S100A8, and S100A9 in the prepared samples were measured by enzyme-linked immunosorbent assay (ELISA). The degree of occurrence was evaluated by measuring the absorbance at 450 nm with an ELISA reader and then quantifying the cytokine concentration using a standard curve.

The experimental results are shown in FIG. 7a-7d.

2-6. Western Blot Analysis

Skin tissue was dissolved in a lysis buffer (150 mM NaCl, 50 mM Tris-HCl, 1 mM EDTA, 50 mM NaF, 10 mM $Na_4P_2O_7$, 1% IGEPAL, 2 mM $Na_3VO_4$, 0.25% protease inhibitor cocktail, and 1% phosphatase inhibitor cocktail) and a protein assay was conducted. 10 to 25 µg of protein was electrophoresed on 11% SDS-PAGE and then transferred to a nitrocellulose membrane for 2 hours. The membrane was blocked for 1 hour and then detection was performed using antibodies against cFOS, IRF9, IRF1, P-IRF3, IRF3, P-p65, p65, P-ERK and ERK.

Figure 8:
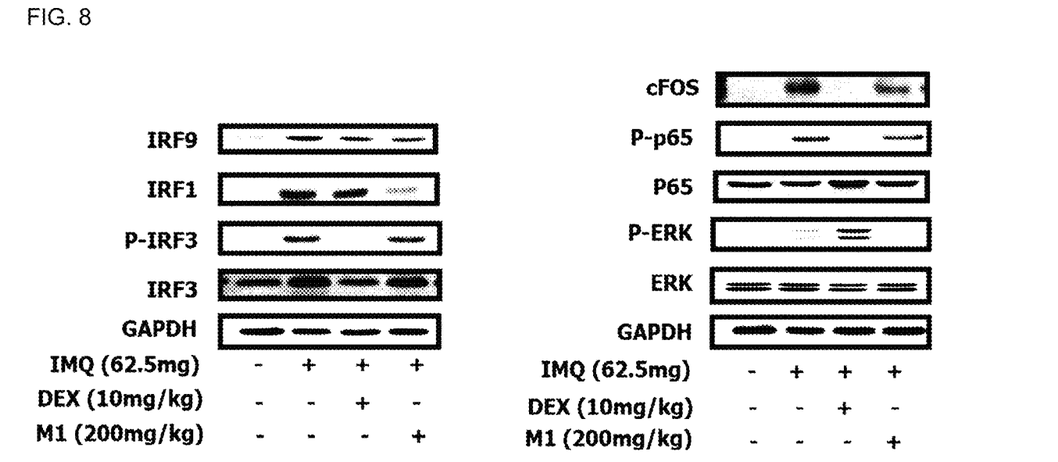
FIG. 8 shows a result of Example 2-6 of the present invention.
Figure 9A:
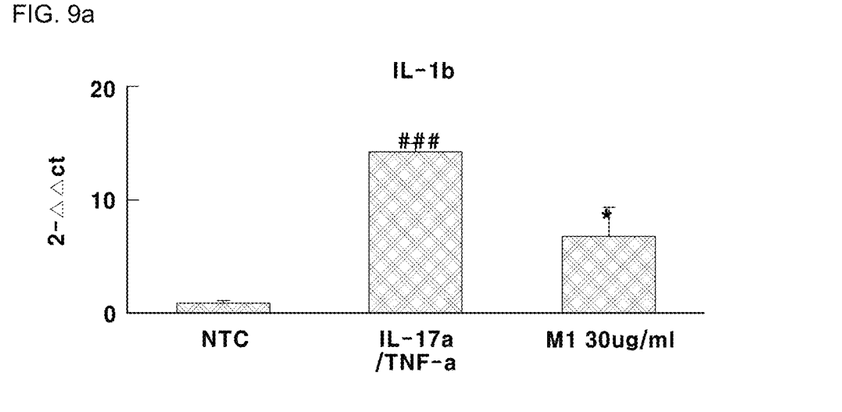
FIG. 9a-9h shows a result of Example 3-3 of the present invention.
Figure 9B:
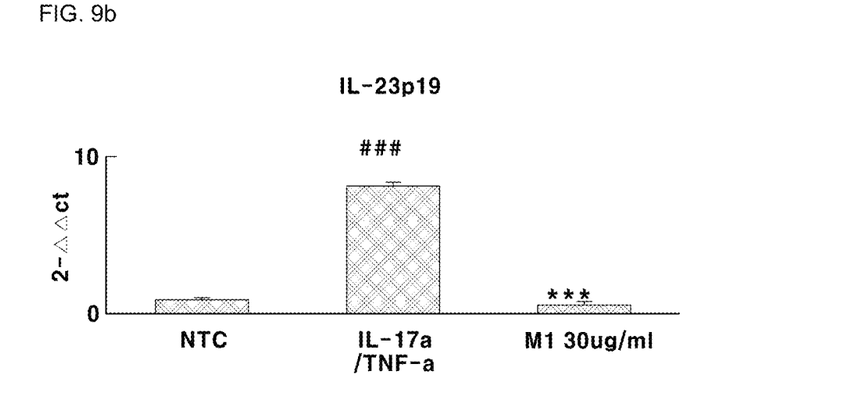
Figure 9C:
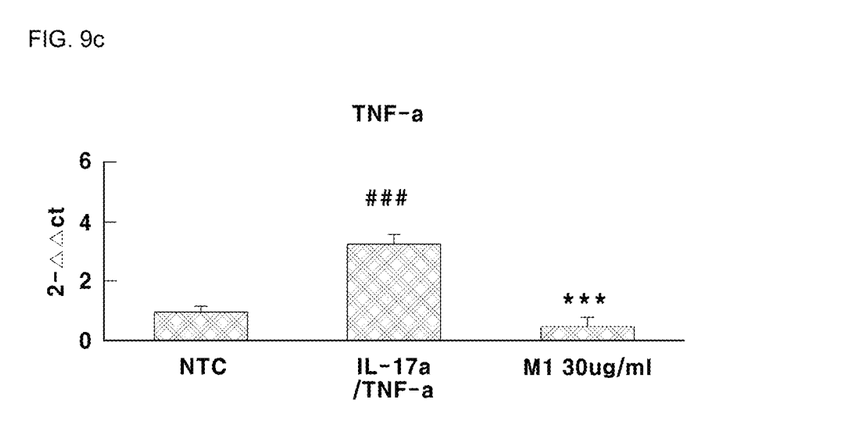
Figure 9D:
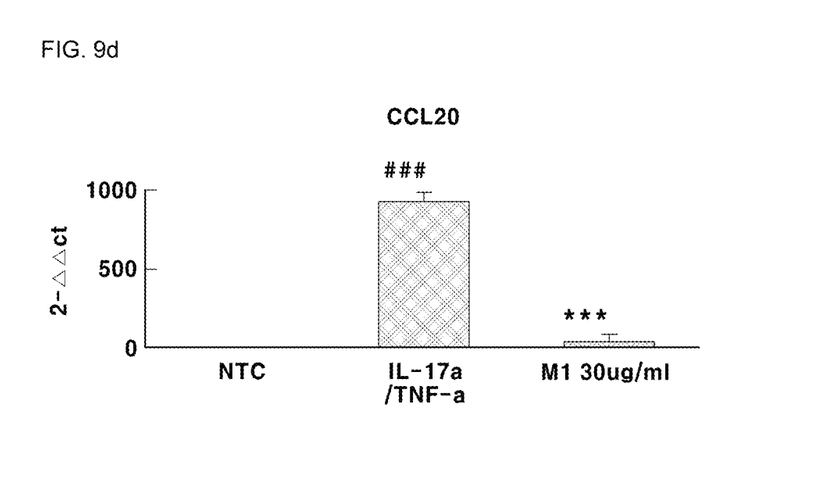
Figure 9E:
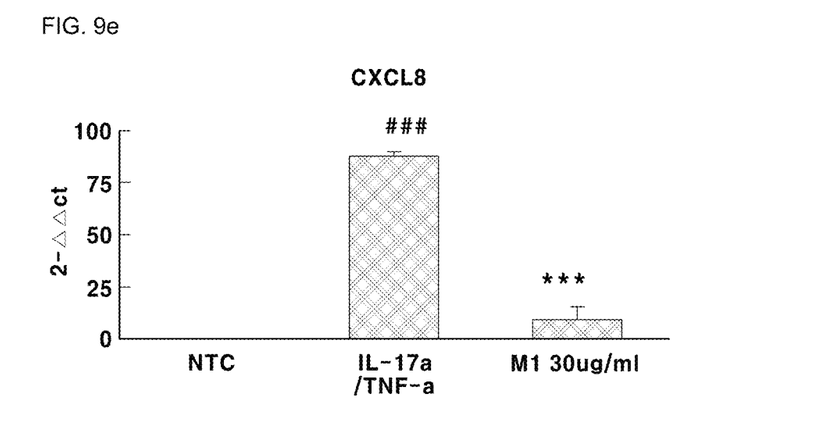
Figure 9F:
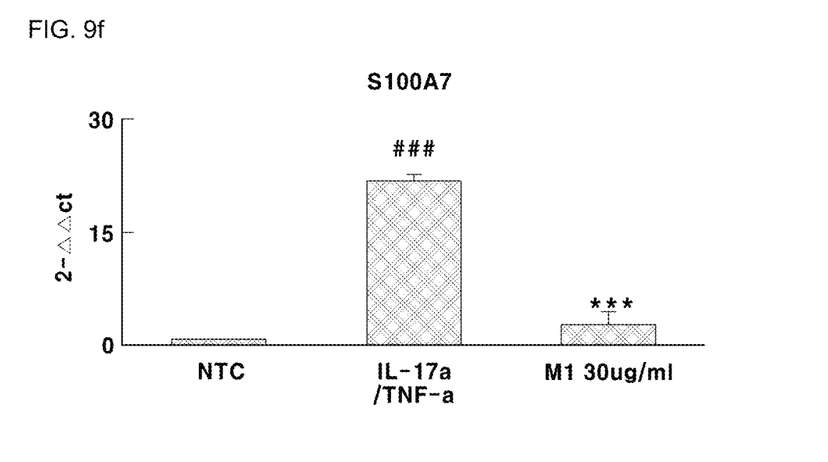
Figure 9G:
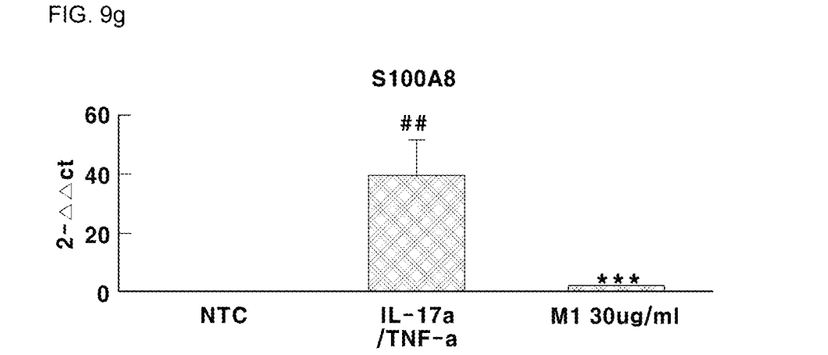
Figure 9H:
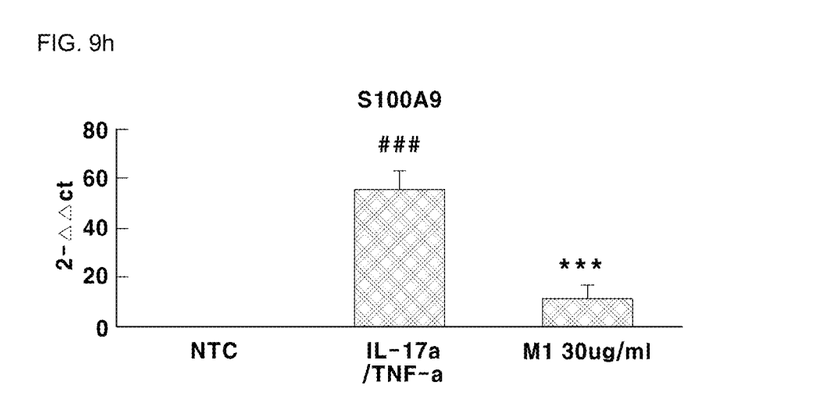

The experimental results are shown in FIG. 8.

Example 3. Determination of Psoriasis Amelioration Effect on Protein Level Through Cell Experiments 3-1. Cells and Cell Culture The cells used in the experiment were HaCaT obtained from the Korea Cell Line Bank. The cells were continuously sub-cultured at intervals of 2 to 3 days in an incubator at 37° C. and 5% $CO_2$ in Dulbecco's modified eagle medium (DMEM) supplemented with 10% (V/V) fetal bovine serum (FBS) and 1% penicillin-streptomycin solution.

3-2. Treatment with Extract Samples

The cells were seeded on a 6-well plate at a density of $5 \times 10^5$ cells/well and stabilized, and then each well was treated with a solution of the extract in serum-free culture and cultured for 24 hours, after which the medium was removed and PBS was added so as to cover a part of the cells, and then IL-17a/TNF-α was further added thereto.

3-3. Measurement of IL-1β, IL_23p19, TNF-α, CCL20, CXCL8, S100A7, S100A8 and S100A9 by Enzyme Immunoassay (ELISA)

HaCaT cells were treated with the extract and IL-17a/TNF-α and then cultured for 38 hours, and then the culture solution was collected and centrifuged at 13,000 rpm for 10 minutes, and then only the supernatant was collected, and the concentrations of IL-1β, IL_23p19, TNF-α, CCL20, CXCL8, S100A7, S100A8, and S100A9 were measured using an enzyme-linked immunosorbent assay (ELISA) kit.

The experimental results are shown in FIG. 9a-9h.

Hereinafter, an example of the formulation of the composition according to the present invention will be described, but the example is provided only for illustration of the present invention, and should not be construed as limiting the scope of the present invention.

[Formulation Example 1] Preparation of Pills

30% by weight of the extract of Example 1, 30% by weight of corn starch, 20% by weight of glycerin, and 20% by weight of a sorbitol powder were mixed, and a pill was prepared using a pill-making machine. The final weight of the ingredients was 3.5 g.

[Formulation Example 2] Preparation of Tablets

30% by weight of the extract of Example 1, 20.5% by weight of lactose, 20% by weight of dextrin, 20% by weight of a maltitol powder, and 7% by weight of a xylitol powder were mixed and granulated using a fluid bed dryer, and then 2.5% by weight of sugar ester was added thereto and tableted with a tablet press. The final weight of the ingredients was 2 g.

[Formulation Example 3] Preparation of Granules

30% by weight of the extract of Example 1, 5% by weight of xylitol, and 65% by weight of isomalt were mixed, formed into granules using a fluid bed granulator, and then charged in a bag. The final weight of the ingredients was 2 g.

[Formulation Example 4] Preparation of Injection

An injection was prepared by a conventional method in accordance with the composition shown in Table 1 below.

TABLE 1

| Mixed ingredients | Content |
| --- | --- |
| Example 1 | 10-50 mg |
| Sterile distilled water for injection | Appropriate amount |
| pH adjuster | Appropriate amount |

[Formulation Example 5] Preparation of Health Food

A health food was produced by a conventional method in accordance with the composition shown in Table 2 below.

TABLE 2

| Mixed ingredients | Content |
| --- | --- |
| Example 1 | 20 mg |
| Vitamin A acetate | 70 µg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinic acid amide | 1.7 mg |
| Folic acid | 50 µg |
| Calcium pantothenate | 0.5 mg |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

[Formulation Example 6] Preparation of Health Drink

A health drink was produced by a conventional method in accordance with the composition shown in Table 3 below.

TABLE 3

| Mixed ingredients | Content |
| --- | --- |
| Example 1 | 1000 mg |
| Citric acid | 1000 mg |
| Oligosaccharide | 100 g |
| Taurine | 1 g |
| Distilled water | Balance |

As is apparent from the foregoing, the composition according to an embodiment of the present invention can be used to prevent, alleviate or treat psoriasis. That is, the composition can significantly decrease skin moisture loss due to psoriasis, increase skin moisture, and significantly inhibit a change in skin thickness and an inflammatory reaction.

The effects of the present invention are not limited to those mentioned above. It should be understood that the effects of the present invention include all effects that can be inferred from the description of the present invention.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for ameliorating or treating a psoriasis of a subject in need thereof, wherein the method consists essentially of administering an effective amount of *Dianthus superbus* L. extract to the subject;
    wherein the *Dianthus superbus* L. extract is a methanol extract;
    wherein the *Dianthus superbus* L. extract is an extract of the above-ground portion of *Dianthus superbus* L., and
    wherein the *Dianthus superbus* L. extract ameliorates or treats psoriasis by inhibiting at least one inflammatory cytokine selected from the group consisting of IL-1βB, IL-23p19, TNF-α, CCL20, CXCL8, S100A7, S100A8, and S100A9.

2. The method according to claim 1, wherein the *Dianthus superbus* L. extract ameliorates or treats psoriasis by reducing skin moisture loss due to psoriasis, increasing skin moisture, reducing a change in skin thickness due to psoriasis, or reducing a size of a skin area exhibiting redness due to psoriasis.

3. The method according to claim 1, wherein the *Dianthus superbus* L. extract is administered in a form of a pharmaceutical composition.

4. The method according to claim 2, wherein the *Dianthus superbus* L. extract is administered in a form of a health functional food.

5. The method according to claim 2, wherein the *Dianthus superbus* L. extract is administered in a form of a pharmaceutical composition.

6. The method according to claim 2, wherein the *Dianthus superbus* L. extract is administered in a form of a functional cosmetic composition.

\* \* \* \* \*